US 7,304,259 B2

(12) United States Patent
Schwarz et al.

(10) Patent No.: US 7,304,259 B2
(45) Date of Patent: Dec. 4, 2007

(54) MAIL PROCESSING SYSTEM WITH MULTILEVEL CONTAMINANT DETECTION AND STERILIZATION

(75) Inventors: Wolfgang Schwarz, Arlington, TX (US); Michael Carpenter, Arlington, TX (US); John J. Mampe, Fort Worth, TX (US)

(73) Assignee: Siemens Energy & Automation, Inc., Alpharetta, GA (US)

( * ) Notice: Subject to any disclaimer, the term of this patent is extended or adjusted under 35 U.S.C. 154(b) by 594 days.

(21) Appl. No.: 10/287,445

(22) Filed: Nov. 1, 2002

(65) Prior Publication Data

US 2003/0145664 A1 Aug. 7, 2003

Related U.S. Application Data

(60) Provisional application No. 60/335,741, filed on Nov. 1, 2001.

(51) Int. Cl.
*B07C 5/00* (2006.01)
(52) U.S. Cl. .................. 209/584; 422/22; 422/28; 700/225; 209/509; 209/900
(58) Field of Classification Search .............. 422/22, 422/28, 186.3; 73/863.22; 436/104; 209/900; 700/225
See application file for complete search history.

(56) References Cited

U.S. PATENT DOCUMENTS

| 5,364,645 | A | 11/1994 | Lagunas-Solar et al. .... 426/248 |
| 6,331,244 | B1 | 12/2001 | Lewis et al. ............. 205/777.5 |
| 6,765,490 | B2 * | 7/2004 | Lopez et al. ................ 340/632 |
| 6,887,710 | B2 * | 5/2005 | Call et al. ..................... 436/53 |
| 2002/0124664 | A1 | 9/2002 | Call et al. |
| 2002/0126008 | A1 | 9/2002 | Lopez |
| 2002/0150500 | A1 | 10/2002 | Carmen et al. |

(Continued)

FOREIGN PATENT DOCUMENTS

CN 1341456 3/2002

(Continued)

OTHER PUBLICATIONS

"Addressing the Anthrax Threat in the Mailroom Environment," www.bordesgroup.com/anthrax_awareness.htm, Roy N. Bordes, Oct. 15, 2001, 5 pages.

(Continued)

*Primary Examiner*—Gladys JP Corcoran
*Assistant Examiner*—Sean E. Conley

(57) ABSTRACT

A method of sorting mail according to the invention includes the steps of receiving a plurality of first mail pieces of unknown origin in a first apparatus for bulk processing of the mail pieces, processing the mail pieces in the first apparatus by one of testing the mail pieces to determine if a potentially dangerous microorganism is present, sterilizing the mail pieces to destroy microorganisms on mail pieces, or both, and then if no contamination is detected or if sterilization is carried out, combining first the mail pieces at a later stage of postal processing with second mail pieces from senders identified as having a lesser risk of contamination than the first mail pieces of unknown origin. The invention further provides mail contaminant detection and sterilization systems suitable for use in such a method.

14 Claims, 4 Drawing Sheets

U.S. PATENT DOCUMENTS

| | | |
|---|---|---|
| 2003/0125835 A1* | 7/2003 | William et al. .............. 700/223 |
| 2003/0138344 A1* | 7/2003 | Mielnik et al. ................. 422/2 |
| 2004/0000508 A1* | 1/2004 | Das et al. .................... 209/584 |

FOREIGN PATENT DOCUMENTS

| | | |
|---|---|---|
| DE | 10150346 | 5/2002 |
| WO | WO 00/04372 | 1/2000 |
| WO | WO 01/06239 A2 | 7/2000 |
| WO | WO 01/06244 A2 | 7/2000 |
| WO | WO 01/06253 A2 | 7/2000 |
| WO | WO 00/63673 | 10/2000 |
| WO | WO 00/68670 | 11/2000 |
| WO | WO 01/55701 A1 | 1/2001 |
| WO | WO 01/55702 A1 | 1/2001 |
| WO | WO 01/55703 A1 | 1/2001 |
| WO | WO 01/55704 A1 | 1/2001 |

OTHER PUBLICATIONS

"Securing the Postal Front," Edward L. Hudgins, www.nationalreview.com, Oct. 22, 2001, 2 pages.

* cited by examiner

MAIL PROCESSING SYSTEM WITH MULTILEVEL CONTAMINANT DETECTION AND STERILIZATION The application claims priority of U.S. Provisional Application No. 60/335,741, filed Nov. 1, 2001.

TECHNICAL FIELD

The invention relates to mail sorting and handling systems, apparatus and methods and in particular to mail handling methods, systems and apparatus utilizing testing and sterilization apparatus to detect and eradicate potentially dangerous pathogens from mail pieces during the mail collection and sorting process.

BACKGROUND OF THE INVENTION

Recently the United States Postal Service (USPS) has recognized the need for techniques to sterilize the mail to prevent the mail from being used to perpetrate acts of bio-terrorism by sending pathogen-containing mail pieces through the mail. In order to counter the threat of exposing postal services employees and mail recipients from the threat of anthrax and/or other pathogens, the USPS has taken steps at great expense to divert mail destined for certain U.S. government agencies for decontamination. However, the processes applied to date have involved mass irradiation of large volumes of mail pieces without consideration of the risk potential associated with different categories of mail. Further, since the sterilization techniques utilized to date were adopted in haste to deal with an emergency situation, the processes and apparatus utilized to sterilize mail have been inefficient and in some cases overdone, resulting in discolored and damaged mail. The present invention addresses systems, methods and apparatus for testing and decontaminating the huge volume of mail handled by the USPS in a more efficient practical manner, taking into account the risk factors associated with different categories of mail.

An electron beam emitter is a device that generates electrons in a vacuum environment, accelerates them to over half the speed of light, and allows the electrons to exit the vacuum chamber through a thin electron-permeable membrane. The use of such devices for sanitization has been suggested; a smaller version of such a device is described in Avnery U.S. Pat. No. 5,962,995, issued Oct. 5, 1999, the entire contents of which are incorporated by reference herein for all purposes.

SUMMARY OF THE INVENTION

A method of sorting mail according to the invention includes the steps of receiving a plurality of first mail pieces of unknown origin in an apparatus for bulk processing of the mail pieces, processing the mail pieces in the bulk processing apparatus by one of testing the mail pieces to determine if a potentially dangerous microorganism is present, sterilizing the mail pieces to destroy microorganisms on mail pieces, or both and then if no contamination is detected or if sterilization is carried out, combining the first mail pieces at a later stage of postal processing with second mail pieces identified as having a lesser risk of contamination than the first mail pieces of unknown origin. Processing the mail pieces in the bulk processing apparatus preferably comprises testing the mail pieces to determine if a potentially dangerous microorganism is present, with or without subsequent sterilization.

The invention further provides an apparatus for decontaminating a singulated stream of mail pieces. Such an apparatus includes a decontamination chamber constructed from a radiation blocking material to contain radiation emitted in the chamber, a decontamination conveyor for conveying the stream of mail pieces along a central path through the chamber, a first generator positioned in the decontamination chamber and oriented to emit electromagnetic radiation in a first direction substantially perpendicular to the singulated stream of mail pieces, and a second generator positioned in the decontamination chamber and oriented to emit electromagnetic radiation in a second direction substantially perpendicular to the singulated stream of mail pieces. The first and second generators are preferably in offset positions and face in opposite directions in a manner effective to irradiate opposite sides of each mail piece.

The invention also provides an apparatus for testing a group of mail pieces or similar objects for contamination. The apparatus includes a test chamber for receiving the mail pieces and a sensor positioned in the test chamber for detection of one or more target contaminant substances on the mail pieces. An agitator mechanism may be positioned to agitate the mail pieces while within the test chamber to an extent effective to dislodge the target contaminant into air within the chamber, and the sensor is preferably of a type effective to detect an air borne target contaminant. An air circulation system is preferably also provided.

The present invention also contemplates a method for decontamination of currency, in the event such problems arise is future. The method comprises feeding currency to a decontamination system, and then decontaminating the currency with the decontamination system. In the case of paper currency, it is preferred to irradiate opposite side faces of each piece of paper currency in a manner effective to kill a target microorganism. These and other aspects of the invention are discussed further in the detailed description that follows.

BRIEF DESCRIPTION OF THE DRAWINGS

In the accompanying drawings, wherein like numerals denote like elements.

DETAILED DESCRIPTION

Figure 1:
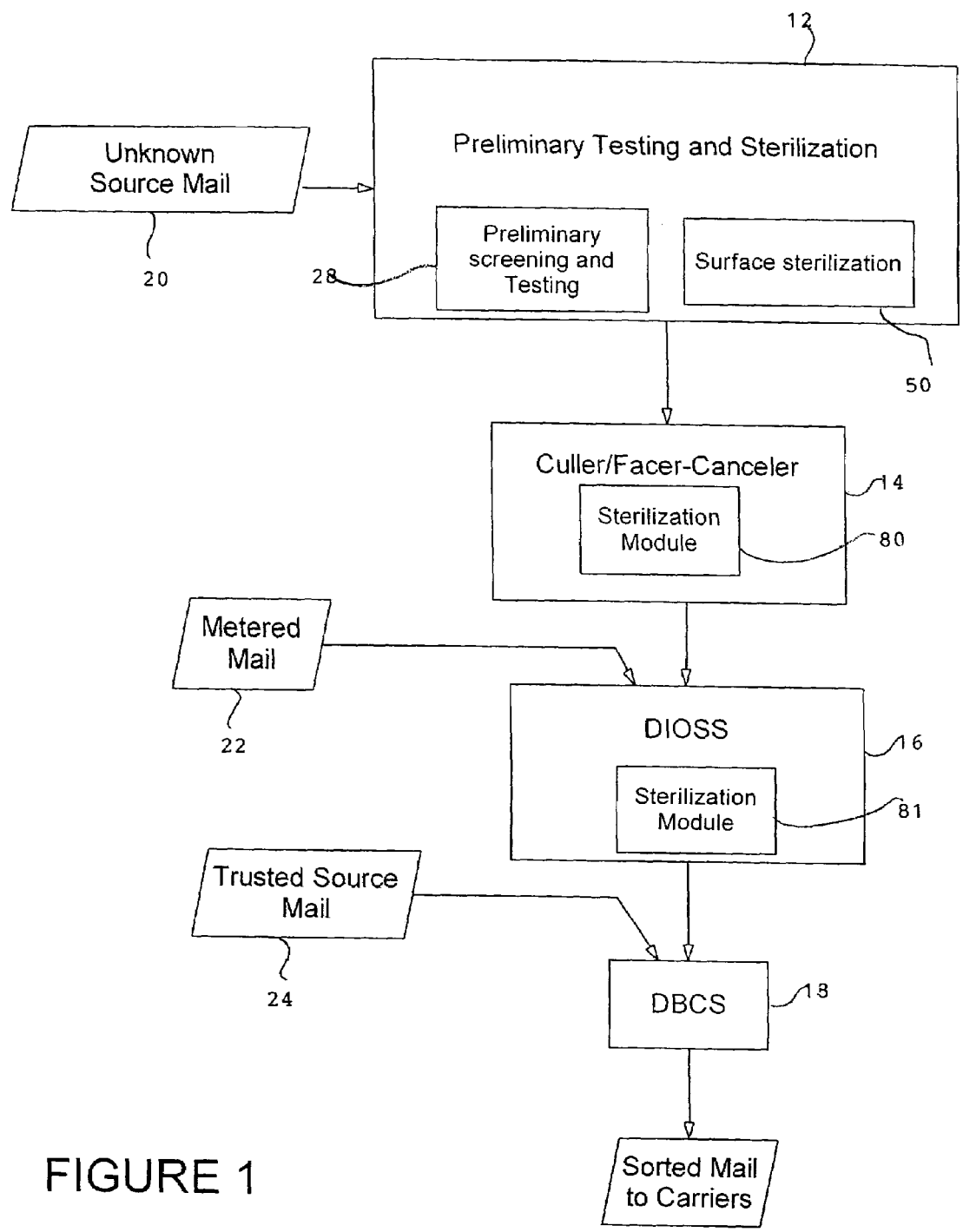
FIG. 1 is a schematic representation of a mail processing system according to the invention

Referring to FIG. 1 a mail collection and distribution system 10 according to the invention receives mail from for processing and delivery from multiple sources. Mail system 10 includes one or more preliminary testing and sterilization modules 12, culling modules 14, Delivery Bar Code Sorter with Optical Character Reader, Input Subsystem, and Output Subsystem 16 (DIOSS) and delivery bar code scanners 18 (DBCS) through which mail is processed and sorted according to a method of the invention. Culling modules 14, DIOSS 16 and DBCS 18 each comprise one or a combination of known pieces of mail handling equipment that are currently used in the United States Postal Service (USPS). Other known postal machines that perform the same or similar functions at each stage of the postal collection and distribution process may also be used.

In accordance with the invention, mail is classified into different categories based upon an assessment of the risk of mail originating from different sources being used as a means of distributing dangerous pathogens. The highest risk level is associated with unknown source mail 20 which is collected from residences, mail drop boxes, business addresses and similar locations and may included mixed mail pieces such as small packages, oversized items along with letter mail. Unknown source mail is believed to have the highest risk of contamination with a pathogen since the source of the individual mail pieces is unknown and to a large extent, undeterminable. For example, the source of a contaminated mail piece dropped in a publically accessible mail drop box with a fictitious or non-existent return address is virtually impossible to determine unless the identity of the depositor can be determined through extrinsic methods such as fingerprints. Due to the relatively high risk level presented by unknown source mail 20, it is highly desirable to test and optionally sterilize unknown source mail 20 to eliminate the possibility of exposing mail handlers and the public to dangerous pathogens that may be present in or on mail pieces comprising unknown source mail 20 at the earliest feasible point in the mail collection and handling process.

Metered mail 22 is collected from businesses, presort mail handlers and similar organizations that generate and/or process sufficient mail to warrant metering. The risk of contamination of metered mail is considered to be less than unknown source mail insofar as the source of the mail can be more readily be determined. However, there is still believed to be a risk since in some cases the entity that meters the mail, for example a private presort company, is not the entity that produces the mail. Thus, while it is desirable to sterilize metered mail 22, the risk associated with metered mail does not warrant the same level of precautionary measures as does unknown source mail 20.

Trusted source mail 24 is collected from high-volume mail generators such as bulk mailers, government agencies, private mail processors and similar organizations. Trusted source mail is considered to represent virtually no risk of contamination since the production and handling of these mail pieces is largely automated, and conducted by a single entity, affording little opportunity for intentional contamination of mail pieces. Since the threat level associated with trusted source mail 24 is considered virtually non-existent, precautionary measures such as testing and sterilization prior to processing are not considered necessary.

Since each of the above categories of mail represents a different threat level with respect to possible contamination, it is appropriate to utilize different techniques to minimize the threat to mail handlers and the public of exposure to pathogens. Thus, in the mail processing system illustrated in FIG. 1, unknown source mail 20, which represents the greatest risk factor is tested and/or sterilized in primary test and/or sterilization module 12 upon collection. Preliminary testing and sterilization module 12 is designed primarily to detect and/or eradicate potentially harmful microorganisms contaminating the exterior surfaces of the unknown source mail 20 mail pieces. Preliminary testing and sterilization module 12 represents a variety of possible testing and/or decontamination devices that may be stationary installations at a local post office or mail collection site or mobile units, for example mounted on a truck that picks up mail from carriers and deposit locations. The particular type of preliminary testing and sterilization module utilized in a given application will depend largely upon the volume and type of mail collected in the particular geographic area served. If module 12 is to be located at a USPS facility, it is preferably located in a building for incoming mail that is separate from downstream processing systems in order to minimize the amount of cleanup if a contaminant is detected, requiring sterilization of the entire area. In such a case, mail loaded onto a belt conveyor for transport through module 12 is then transported to the adjoining building through a tube or tunnel connecting the two buildings which houses the conveyor, and wherein a positive air pressure in maintained in the tube to prevent contamination of the downstream building.

Figure 2:
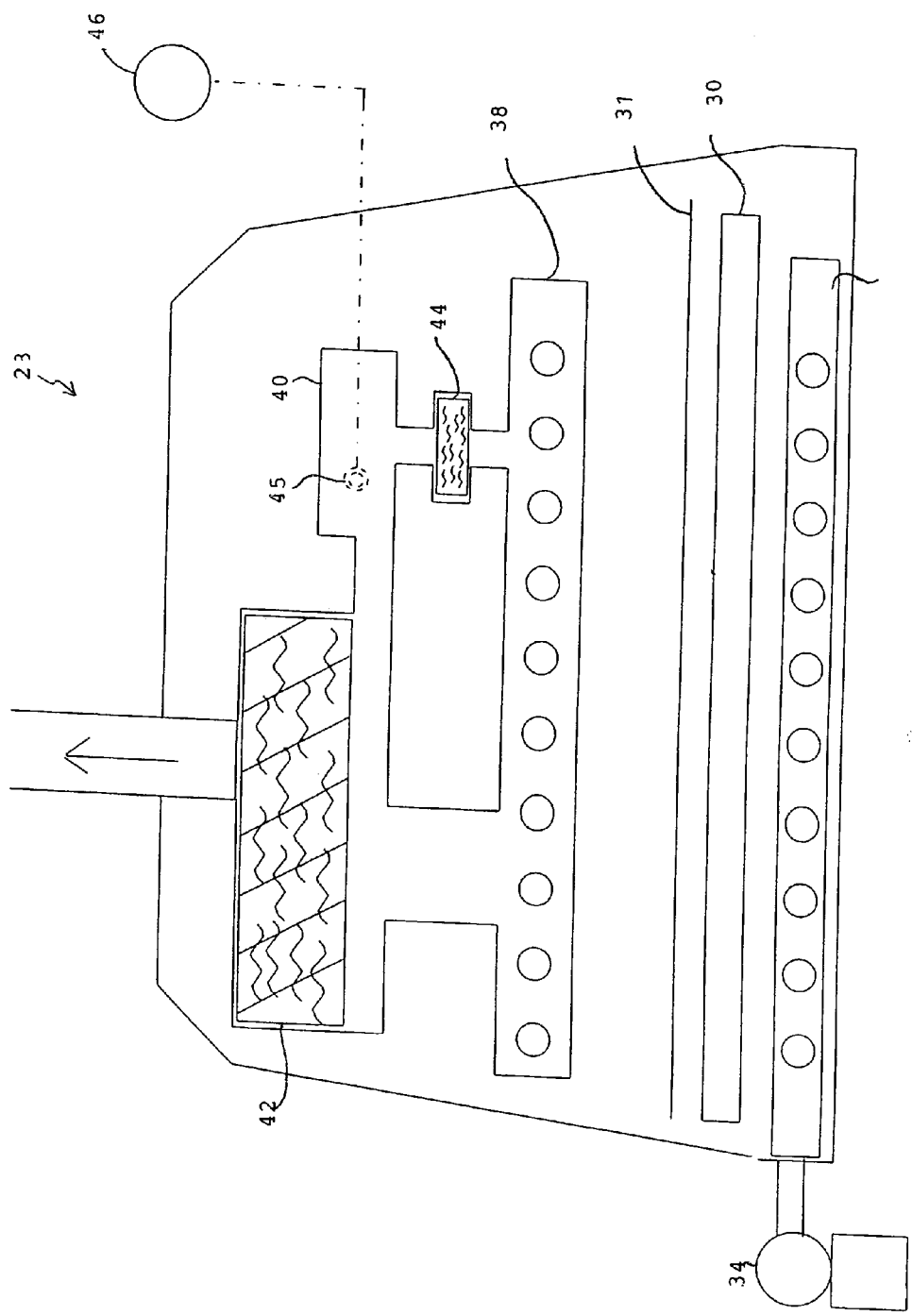
FIG. 2 is a schematic representation of the preliminary testing module of FIG. 1.

As illustrated in FIG. 2, in one variation, preliminary testing and sterilization module 12 comprises a screening and test unit 28 adapted for batch processing of mail pieces. In this variation, module 12 comprises a test chamber 32, a compressor 34, distribution plenum 36, collection plenum 38, detection apparatus 40 and discharge filter 42. Preferably, preliminary testing and sterilization module 12 is provided with means such as a shaker/vibrator 30 for agitating the mail pieces processed in module 12. It will be appreciated that test unit 28 may, of course, be installed on a mobile unit that may be routed to various locations where source mail 20 is received from carriers or at mail collection points. An optional belt conveyor 31 conveys mail into and out of chamber 32, either continuously or batchwise, through entry and exit openings.

Once the collected unknown source mail is deposited or conveyed into chamber 32, compressor 34 is energized to pump air into test chamber 32 through distribution plenum 36 and maintain a steady air flow. Simultaneously, shaker/feeder 30 is activated to shake the mail pieces on conveyor 31, dislodging contaminants from the mail pieces. Compressed air entering test chamber 32 through distribution plenum 36 picks up contaminants dislodged from the mail pieces and carries the contaminants out of the chamber through collection plenum 38.

A biohazard detection unit 40 samples the air passing through collection plenum 38 to detect the present of hazardous or potentially hazardous microorganisms. In one variation, detection unit 40 comprises a test filter 44, sized to remove particles having a size greater than that of the microorganisms and/or carrier particles used to disperse the microorganisms. After filtering, the air sample is then passed through an optical detector 45 to determine if particles pre-identified as potentially dangerous are present in the air. Methods used to identify such particles may vary as described further below, but in general it is desirable to characterize the target cells or particles as specifically as possible to avoid a high rate of false positive readings.

According to some optical methods, particle reflectance is measured. U.S. Pat. No. 5,471,299 above describes an imaging system capable of recording both the radial and azimuthal (about the illuminating beam axis) variations in the pattern of scattered light from individual particles carried in a sample airflow. Particles are classified on the basis of their shape (whether, for example, spherical, cuboidal, flake-like, or fibrous) as well as on their size, the latter being derived from an assessment of the total scattered intensity. Thus loose powder used as a carrier for anthrax spores could be identified.

Spectroscopy may be undertaken in unit 40 to detect for absorption spectra characteristic of known target pathogens such as anthrax. See, for example, U.S. Pat. No. 5,512,490 which describes an optic sensing apparatus and methodology for detecting and evaluating one or more analytes or ligands of interest, either alone or in admixture. The optic sensor of the system is comprised of a supporting member and an array formed of heterogeneous, semi-selective thin films which function as sensing receptor units and are able to detect a variety of different analytes and ligands using spectral recognition patterns. The entire contents of U.S. Pat. Nos. 5,512,490, 5,471,299, 5,320,814, 5,409,666, 5,382,512, 4,818,103, 5,093,866, and 4,606,636, describing systems for identifying unknown particles, are incorporated herein by reference for all purposes. PCT publication WO 00/63673 discloses a further system for identifying the size, shape and fluorescence of fluidborne particles.

If it is desired to identify specific microorganisms that pose a threat, such as bacteria, spores and viruses, then detection apparatus 40 may incorporate an bioassay system therein, generally wherein a reaction can occur between a pair of specifically binding substances such as an antigen and an antibody. One substance of the pair is presented on a solid phase such as a polymeric microbead. If the target substance is present in the sample, a specific binding reaction will occur and the reaction is then detected by any of a variety of known means. Almost all such systems operate in an aqueous phase, and as such it may be necessary to pass the potentially contaminated air from plenum 38 through an exchanger wherein airborne particles enter into the aqueous phase and may be tested for, optionally with further processing to break whole cells down into components substances.

Bioassay systems are well known and effective, but are usually run in a lab environment. Recent efforts have been directed towards making such systems more useful for detecting multiple target substances at a time with an electronic endpoint, that is, a change in properties of the system that can be measured electronically without resort to means such as chemical labels to detect that a reaction has occurred. Detection unit 40 accordingly may comprise an electronic "nose," "tongue" or similar device adapted to sense the presence of particular microorganisms either directly or indirectly through detection of a substance associated with the potentially dangerous microorganisms, such as a carrier powder or a byproduct produced by the microorganism. These devices generally comprise a substance that evidences a electronically measurable change upon reacting with the microorganism or a material associated with the microorganism. The substance may change color, conductivity or fluoresce upon reacting with a suspicious substance. A number of sensor systems for detection of such substances in a fluid have been proposed, including those described in PCT Publication Nos. WO0155704, WO0155703, WO0155702, WO0155701, WO0106253, WO0106244, WO0106239, WO0068670, and WO0004372.

For example, PCT Publication Nos. WO0106239 provides a system for detecting analytes that includes a light source, a sensor array, and a detector. The sensor array is formed of a supporting member which is configured to hold a variety of chemically sensitive particles in an ordered array. The particles create a detectable signal in the presence of an analyte. The particles may produce optical (e.g., absorbance or reflectance) or fluorescence/phosphorescent signals upon exposure to an analyte. Examples of such particles include functionalized polymeric beads, agarose beads, dextrose beads, polyacrylamide beads, control pore glass beads, metal oxides particles (e.g., silicon dioxide ($SiO_2$) or aluminum oxides ($Al_2O_3$)), polymer thin films, metal quantum particles (e.g., silver, gold, platinum, etc.), and semiconductor quantum particles (e.g., Si, Ge, GaAs, etc.). A detector (e.g., a charge-coupled device"CCD") is positioned below the sensor array to allow for data acquisition. Light originating from the light source may pass through the sensor array and out through the bottom side of the sensor array. Light modulated by the particles may pass through the sensor array and onto the proximally spaced detector. Evaluation of the optical changes may be completed by visual inspection or by use of a CCD detector by itself or in combination with an optical microscope. A microprocessor may be coupled to the CCD detector or the microscope.

A fluid delivery system may be coupled to the supporting member of the sensor array to introduce samples into and out of the sensor array. In an embodiment, the sensor array system includes an array of particles. The particles may include a receptor molecule coupled to a polymeric bead. The receptors are chosen for interacting with analytes. This interaction may take the form of a binding/association of the receptors with the analytes. The supporting member may be made of any material capable of supporting the particles, while allowing the passage of the appropriate wavelengths of light. The supporting member may include a plurality of cavities. The cavities may be formed such that at least one particle is substantially contained within the cavity.

A high sensitivity CCD array is used to measure changes in optical characteristics which occur upon binding of the biological/chemical agents. The CCD arrays may be interfaced with filters, light sources, fluid delivery and micromachined particle receptacles to create a functional sensor array. Data acquisition and handling is performed with existing CCD technology. CCD detectors may be configured to measure white light, ultraviolet light or fluorescence. Other detectors such as photomultiplier tubes, charge induction devices, photo diodes, photodiode arrays, and microchannel plates may also be used. A particle of this system possesses both the ability to bind the analyte of interest and to create a modulated signal. The particle has receptor molecules which posses the ability to bind the analyte of interest and to create a modulated signal. Alternatively, the particle may include receptor molecules and indicators.

Upon binding the analyte of interest, the receptor molecule causes the indicator molecule to produce the modulated signal. The receptor molecules may be naturally occurring or synthetic receptors. Some examples of natural receptors include, but are not limited to, DNA, RNA, proteins, enzymes, oligopeptides, antigens, and antibodies. Either natural or synthetic receptors may be chosen for their ability to bind to the analyte molecules in a specific manner. In one embodiment, a naturally occurring or synthetic receptor is bound to a polymeric bead in order to create the particle. The particle, in some embodiments, is capable of both binding the analyte (s) of interest and creating a detectable signal. In some instances, the particle creates an optical signal when bound to an analyte of interest.

A variety of natural and synthetic receptors may be used. The synthetic receptors may come from a variety of classes including, but not limited to, polynucleotides (e.g., aptamers), peptides (e.g., enzymes and antibodies), synthetic receptors, polymeric unnatural biopolymers (e.g., polythioureas, polyguanidiniums), and imprinted polymers. Polynucleotides are relatively small fragments of DNA which may be derived by sequentially building the DNA sequence. Peptides include natural peptides such as antibodies or enzymes or may be synthesized from amino acids. Unnatural biopolymers are chemical structure which are based on natural biopolymers, but which are built from unnatural linking units. For example, polythioureas and polyguanidiniums have a structure similar to peptides, but may be synthesized from diamines (i.e., compounds which include at least two amine functional groups) rather than amino acids. Synthetic receptors are designed organic or inorganic structures capable of binding various analytes.

In order to identify, sense, and quantitate the presence of various bacteria using the micromachined sensor, two strategies may be used. First, small molecule recognition and detection may be exploited. Since each bacteria possesses a unique and distinctive concentration of the various cellular molecules, such as DNA, proteins, metabolites, and sugars, the fingerprint (i.e., the concentration and types of DNA, proteins, metabolites, and sugars) of each organism is expected to be unique. Hence, the analytes obtained from whole bacteria or broken down bacteria may be used to determine the presence of specific bacteria. A series of receptors specific for DNA molecules, proteins, metabolites, and sugars may be incorporated into an array. A solution containing bacteria will provide a pattern within the array which may be unique for the individual bacteria. In this manner, the presence of bacteria within a fluid may be determined. Bacteria may be detected as whole entities. To detect, sense, and identify intact bacteria, the cell surface of one bacteria is differentiated from other bacteria. One method of accomplishing this differentiation is to target cell surface oligosaccharides (sugar residues). Each bacterial class (gram negative, gram positive, etc.) displays a different oligosaccharide on their cell surfaces. The oligosaccharide, which is the code that is read by other cells giving an identification of the cell, is part of the cell-cell recognition and communication process. The use of synthetic receptors which are specific for oligosaccharides may be used to determine the presence of specific bacteria by analyzing for the cell surface oligosaccharides.

A system such as the foregoing can be adapted for purposes of the invention to detect for dangerous bacteria, spores or the like. Since such a system is based on specific binding reactions between the target and the receptor, it is less likely to result in false positives than a system based on optical particle recognition, but may be more difficult to implement.

In one variation, detection unit 40 is equipped with an alarm 46 for signaling the presence of a suspicious or potentially hazardous material. Testing and sterilization module 12 may be configured to shut down when alarm 46 indicates the presence of a suspicious material, so that appropriate measures may be taken to deal with the potential threat. For this purpose, and especially if an optical system is used as the first level of screening, a positive result may cause a second, more accurate bioassay to be conducted to confirm that the threat is actual and not a false positive. Air discharged from test unit 28 is first passed through discharge filter 42, such as a HEPA filter, designed to remove particulate matter having a particle size above that associated with a pathogen or pathogen carrier.

Preliminary testing and sterilization module 12 preferably includes a sterilization unit 50 (FIG. 1), designed to sterilize at least the surface of unknown source mail 20 mail pieces prior to sorting. This may be done before or after preliminary screening and testing, in place of such testing, or in response to test results (upon a positive or probable positive detected by test unit 28, sterilization unit 50 is activated, but not otherwise.)

Surface sterilization unit 50 may be located at local post offices where unknown source mail 20 is received from carriers after collection, or at larger collection and sorting centers. In one embodiment, sterilization unit 50 is a bulk sterilization unit which may use a variety of different sterilization techniques to eradicate potentially dangerous pathogens without singulating the mail pieces. In this respect, surface sterilization unit 50 may comprise a chamber for batch treatment of unknown source mail 20 with a disinfecting gas such as ozone capable of destroying pathogens but harmless to the mail. Alternatively, surface sterilization unit 50 may comprise a conveyor or series of conveyors that pass the mail pieces through one or more beams of electromagnetic radiation of sufficient intensity to destroy potentially dangerous microorganisms. The electromagnetic radiation may be X-ray, ultraviolet, UV laser, RF, microwave or other frequency radiation, so long as a dosage of radiation is applied to the mail pieces effective to eradicate any potentially dangerous microorganisms present on the surface of the mail pieces without damaging the mail pieces. To the extent that the selected method can penetrate further than the surface of a mail piece, the method may be effective for sterilizing dangerous microorganisms that might be contained inside a mail piece. High powered radiation, such as high power electron beam irradiation, at this stage is not preferred because it degrades the mail pieces themselves as well as any dangerous microorganisms.

Figure 3:
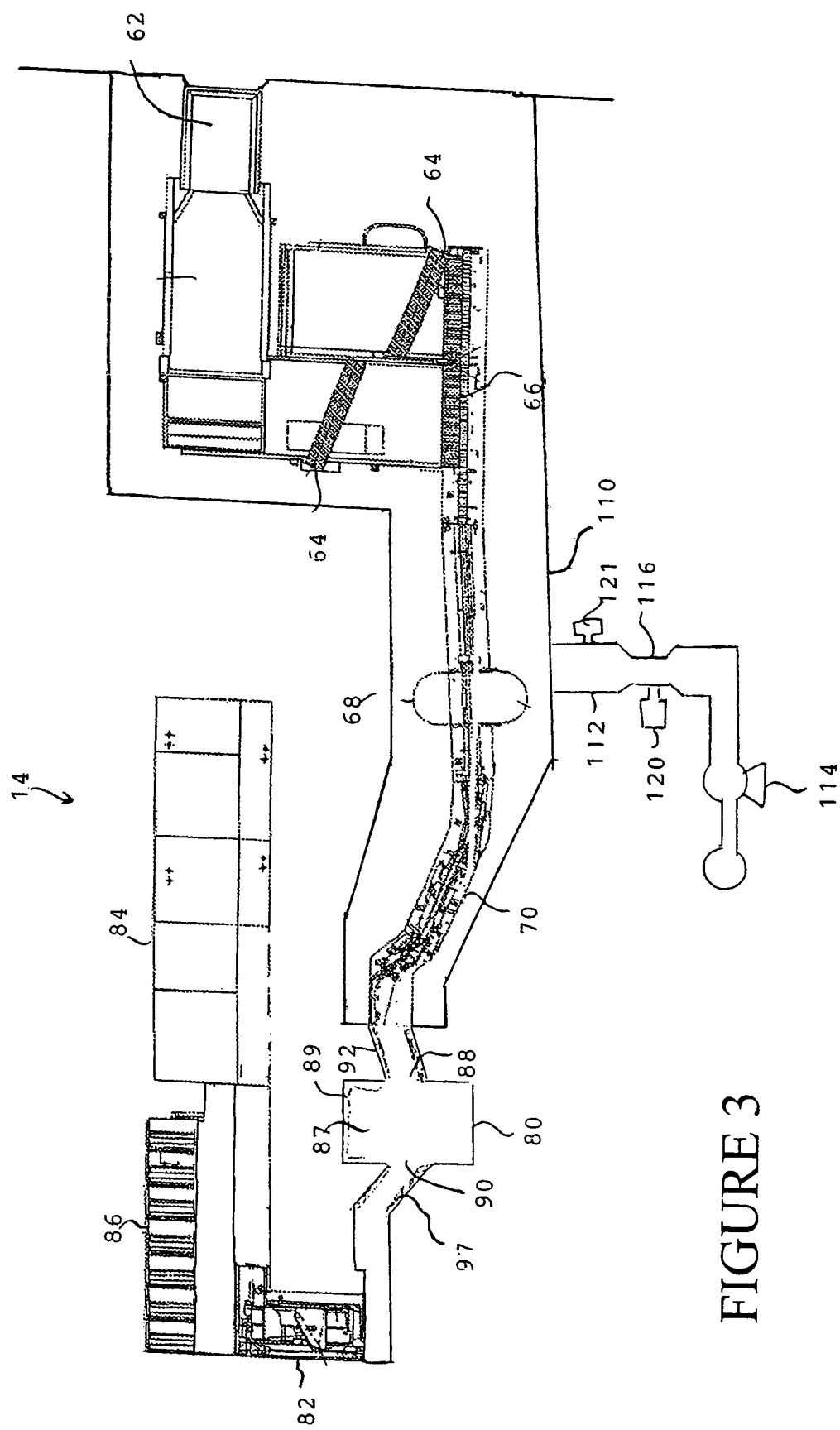
FIG. 3 is a schematic representation of the culling and facing module of FIG. 1.

After testing and/or sterilization in preliminary testing and sterilization module 12, unknown source mail 20 is processed through a modified rough cull and distribution module 14 for separation of flats, parcels and similar items from envelope mail, facing and canceling. Referring to FIG. 3, the rough cull and distribution module comprises an input hopper or chute 62 where mail is deposited, an incline that directs the mail to a plurality of angled rollers 64 which convey the mail pieces to a vertical transport and culler 66 wherein the mail pieces drop into a trough and form a stream of mail pieces 4–5 pieces thick which can then be transported by an upright belt conveyor having a pair of belts.

From culler 66, the mail pieces are transported to flats extractor 68 which removes flats, i.e., items larger than a typical letter such larger envelopes, magazines, and similar items. After the flats have been removed from the mail stream, the mail is singulated, i.e., separated into a stream of envelope size, separated, individual mail pieces, in singulation section 70. The singulated mail stream is conveyed through a sterilization module 80 (FIG. 4) after which the mail stream is successively transported through a buffer feeder 82, a facer and canceler unit 84 to stacker module 86. One or more of the individual components may be equipped with an evacuation hood 110 and air decontaminating unit as hereinafter described. It should be noted that with the exception of the sterilization module 80 and hooded enclosure and air decontamination unit 110, the rough cull and distribution module 14 is a conventional mail processing unit that is well known and widely used in postal facilities.

Figure 4:
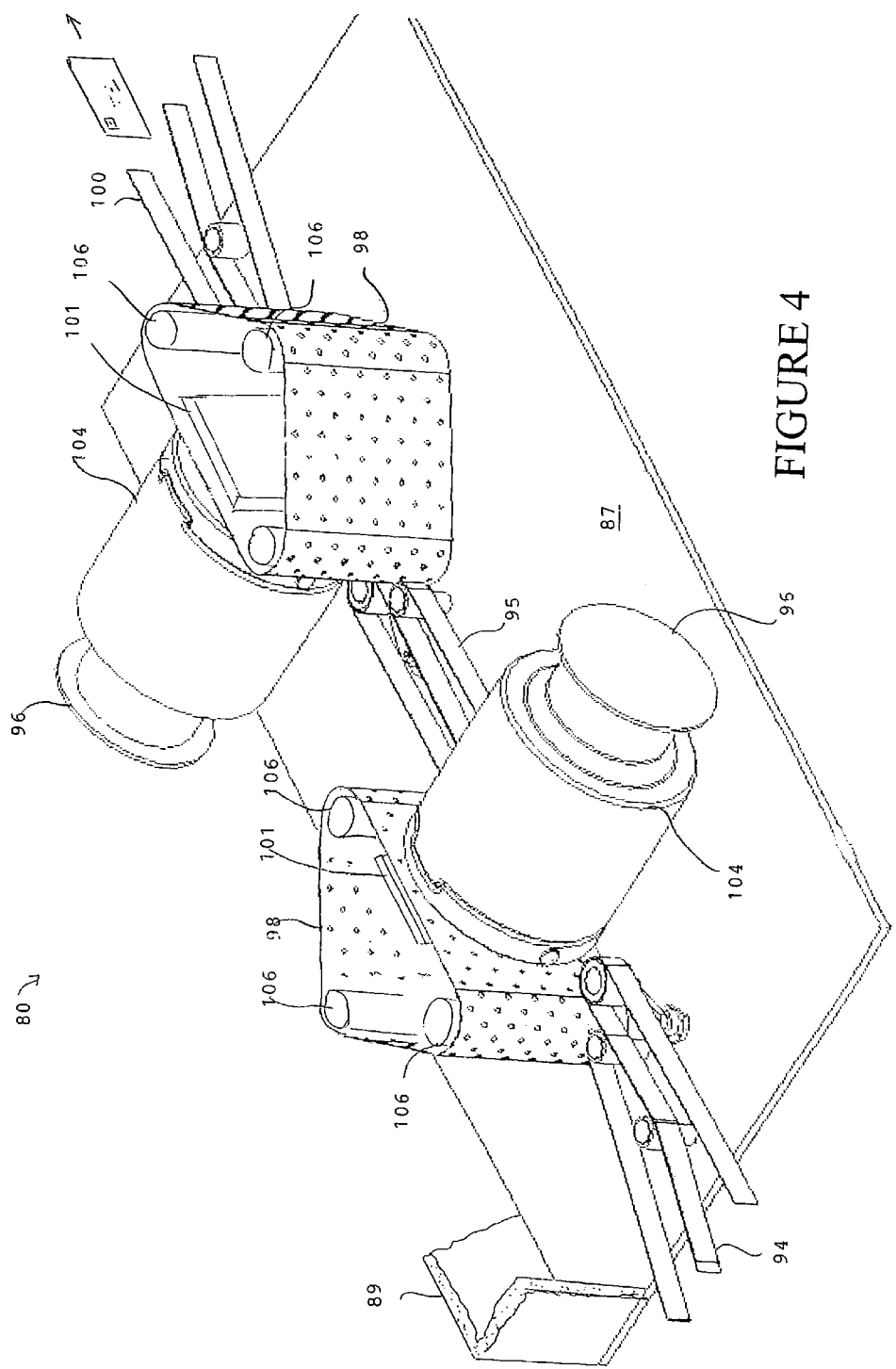
FIG. 4 is a partial perspective view of a sterilization module according to the invention.

Referring now to FIGS. 3 and 4, a radiation sterilization module 80 according to the invention is designed to eradicate potentially dangerous microorganisms contained inside the mail piece in contrast to surface sterilization unit 50 which is designed only to destroy such pathogens on the surface of the mail pieces. Singulated mail is transported to entrance 88 of sterilization module 80 with one or more conventional pinched or opposed belt-type conveyors that convey the mail through a protective angled tunnel-like entry structure 92 constructed of lead or another effective radiation absorbing material to contain radiation used to sterilize the mail pieces. The mail pieces are received in a central decontamination chamber 87, treated with relatively low power e-beams and discharged through exit 90 and angled discharge tunnel 97, which is constructed in the same manner as entrance tunnel 92. As illustrated, tunnels 92 and 97 are angled relative to the transport path of central sterilization tunnel 93 and have a length sufficient to attenuate radiation emitted during the sterilization process. In general, it is preferred that radiation emitted from the e-beam projector be forced to reflect several times (3 or more) off of the lead walls before reaching the open entrance or exit of the tunnels 92, 97. This reduces the energy of such radiation to a harmless level without requiring that module 80 be completely sealed during operation. For this purpose an angle of at least about 10 degrees for each tunnel and a tunnel length of at least about several feet is preferred for the illustrated embodiment using a pair of 125 mV projectors. The walls of tunnels 92, 97 wall 89 of chamber 87 form a continuous structure impervious to the selected radiation type and open only at the far ends of each tunnel 92, 97. In this manner, module 80 can operate continuously as a stream of mail pieces are conveyed through it at high speed.

In accordance with the invention, it is contemplated that electromagnetic radiation across a broad range of frequencies including, but not limited to, RF, microwave, UV, laser, electron beam and x-ray could be used to sterilize the mail pieces. In a preferred embodiment electron beam (e-beam) radiation is used to sterilize mail pieces processed through module 80. Electron beam radiation is generated with an emitter that accelerates electrons in a vacuum to over half the speed of light and allows the electrons to exit the vacuum chamber through a thin electron-permeable membrane. Large-scale E-beam irradiation units are used in food and medical sterilization processes with energies of more than 10 MeV. These machines require thick concrete and/or lead lined walls to shield human operators from x-ray radiation emitted by the irradiation units. Typically the walls are angled, serpentine or curved structures that create multiple reflective surfaces designed to attenuate the intensity of x-rays, reducing the energy of the radiation to a safe level.

A relatively recent development in e-beam technology is a newer, smaller, self-enclosed product such as described in Avnery U.S. Pat. No. 5,962,995, issued Oct. 5, 1999, the entire contents of which are incorporated by reference herein for all purposes. Such an e-beam emitter is manufactured by Advanced Electron Beams, Inc. (AEB) and, while it has the potential for use in sterilization applications, it utilizes less energy, thereby minimizing the amount of potentially harmful radiation generated and minimizing the amount of shielding required to protect personnel. Commercially available AEB units rated at 125 kV are believed suitable for use in connection with sterilization module 80 as described below, however, higher energy units may also be utilized as necessary to provide e-beams with sufficient energy to eradicate any pathogens present in mail pieces of varying thickness. An e-beam projector with an energy rating of 300–500 kV may be useful for this purpose.

Referring now to FIG. 4, sterilization module 80 according to the invention includes a decontamination chamber 87 enclosed with walls 89 formed from a material such as lead and/or concrete capable of blocking radiation emitted during the sterilization process to prevent radiation from escaping into the surrounding work area. Sterilization module 80 also includes an opposed belt input conveyer 94, a pair of staggered, opposed e-beam emitter units 96, an endless perforated conveyor belt 98 positioned in front of each of each emitter 96, an opposed belt transfer conveyor 95 for conveying mail pieces between emitters 96, and an opposed belt exit conveyor 100. Transfer conveyor 95 and perforated belt conveyor belts 98 define a central path through chamber 87 such that the e-beams generated by emitters 96 are substantially perpendicular to the central path along which mail pieces are conveyed.

A vacuum plenum 101 positioned inside of each of belts 98 applies a vacuum through perforations 102 in each of belts 98 to hold mail pieces against the belts as the belts 98 convey mail pieces past each of emitter units 96. Preferably belts 98 are constructed from a radiation resistant material such as a metal, e.g. steel. Each of emitters 96 is provided with a water jacket 104 and connections (not shown) to a source of circulating cooling water for cooling each emitter unit 96 during operation. As shown, belts 98 are arranged around three pulleys 106, at least one of which is driven with a conventional drive unit such as an electric motor (not shown). In one embodiment, cooling water is circulated through the inside one or more of pulleys 106 to cool belt 96 during operation. Preferably, a stand alone electronic control and power supply unit is provide for operation and control of the sterilization unit along with a cooling water circulating pump and heat exchanger to provide cooling water for emitters 96 and belts 98.

As illustrated, emitters 96 are staggered and face in opposite directions. This arrangement allows each emitter 96 to be operated a power level sufficient to generate an e-beam capable of penetrating one-half of the thickness of mail pieces processed through sterilization module 80. In a preferred embodiment, each of emitters 96 is operated at a power level sufficient to generate from about 100 KeV to about 500 KeV, especially 300–500 KeV. Positioning and operating emitters 96 in this fashion reduces the amount of x-ray radiation generated during the process, reducing the amount of shielding required. Operating emitters 96 at a lower power level also reduces the amount of discoloration and other damage mail pieces processed through sterilization unit 80 may suffer. Other advantages of operating at a lower power level include reduced cooling requirements and reduced equipment damage from radiation-induced brittleness and heat. As will be appreciated, sterilization modules 80 may be utilized in a variety of locations in a typical mail processing and sorting facility where a singulated stream of mail pieces may be passed through such a module.

It will also be appreciated that during the culling process, mail pieces are jostled and shaken, presenting the risk that pathogens contained in the mail pieces may be released into the atmosphere, possibly endangering personnel. In one aspect of the invention, one or more of the mail handling devices in culling unit 14 is provided with an air collection hood or enclosure 110 (FIG. 3) operated under negative pressure. Collection hood 110 is connected via a duct 112 to an exhaust fan 114 that maintains a negative pressure to evacuate particulate matter that might be released as mail pieces are processed through culling unit 14. Duct 112 includes a restriction 116 where collected air is conveyed at a velocity such that the flow of air through restriction 116 is laminar. One or more e-beam emitters 120 may be positioned to project e-beams across restriction 116 to destroy any microorganisms that may be present in the collected air, or a suitable filter may be provided. Since the e-beams are not required to penetrate layers of paper, as in the case of sterilization module 80, emitters 120 may be operated at a substantially lower power level than emitters 96. Collection hood 110 preferably comprises an enclosure that seals off the entire front end of the machine, from the chute 62 up to tunnel 92 leading to the decontamination module 80. In this way the potential for contamination resulting from dangerous microorganisms being released from mail pieces during the culling process may be greatly reduced. Input chute 62 may open onto a separate room of the facility that is completely separate from the areas in which downstream processing is conducted. A detection unit 121, similar to unit 40, may be provided in duct 112 to sound an alarm if contamination is detected. Upon such an alarm, operation if culling machine 14 is suspended and decontamination of the outer room adjoining chute 62 may be undertaken, for example, by exposing the entire area to UV light after evacuating all personnel.

Referring again to FIG. 1, after culling and canceling, the letter-sized stream of mail pieces is forwarded to a sorting machine such as a Delivery Bar Code Sorter with Optical Character Reader, Input Subsystem, and Output Subsystem (DIOSS) 16 for a primary sort by, for example, one or more leading zip code numbers. At this point, metered mail 22 which, as noted above, has a lower risk level than unknown source mail 20, is introduced in the mail handling system. DIOSS 16 includes a sterilization module 81 which may be essentially the same as module 80, but positioned immediately downstream from the pick off mechanism of the machine. DIOSS 16 may be enclosed and air-filtered, in whole or in part, to prevent escape of contaminants, in a manner similar to hood 110 described above.

After sterilization, metered mail 22 is read or scanned by a bar code reader and/or OCR reader and then sorted to one of a plurality of pockets according to a sort scheme, all in accordance with conventional operation of a DIOSS machine 16. DIOSS 16 uses one or more bar code scanners, optical character recognition (OCR) readers, image scanners or similar devices to read destination indicia appearing on the mail pieces. The machined scanned date is then processed with one or more computers that utilize the scanned information to complete the preliminary sort of the mail with conventional mail handling equipment. DIOSS 16 also typically includes a printer that can apply a delivery bar code to a mailpiece for downstream sorting and processing, when necessary. The downstream portion of the DIOSS machine 16 is not enclosed on the assumption that any contamination did not survive passage through sterilization unit 81. However, in the event a biohazard sensor such as described in connection with FIG. 2 positioned inside unit 81 detects a hazardous organism in the upstream portion of the system, a similar sensor may be activated in the area surrounding the sorting pockets/output side of DIOSS machine 16 to confirm that the potential hazard did not contaminate that area. An exit side of the enclosure of unit 71 may be left open to permit room air inflow in the vicinity of the e-beam units.

Referring again to FIG. 1, mail pieces scanned and sorted with DIOSS 16 are each directed to one of a plurality of delivery bar code scanners 18 (DBCS) for sorting into delivery order. DBCS 18 is a conventional mail sorting unit including a scanner for reading a delivery bar code from the mail pieces and a plurality of computer controlled conveyors and diverters that sort the mail into a plurality of bins in delivery order. Trusted source mail 24 is introduced into the handling system at this point. Since trusted source mail 24 normally comprises pre-sorted and pre-coded mail pieces, appropriately separated bundles of trusted source mail 24 may be introduced into each DBCS 18 without preliminary sorting through DIOSS 16. Since trusted source mail 24 is deemed to present almost no risk of contamination with a biological agent, sterilization of trusted source mail 24 is not considered desirable or necessary. The mail sorted in carrier delivery order is then distributed to the mail carriers for delivery.

As described herein, the invention provides a integrated multilevel test and sterilization apparatus and method that applies the appropriate level of precautionary measures to mail originating from different sources, each of which represents a different level of threat of transmitting dangerous pathogens. Unknown source mail which represents the highest threat of contamination with a dangerous microorganism is tested and sterilized with the most rigorous precaution steps. Metered mail, which represents a lesser threat is sterilized to eliminate the possibility of contamination, but is not subjected to testing and the precautionary measures employed with unknown source mail. Trusted source mail having little or no possibility of contamination is processed without testing or sterilization. In this manner, the amount of equipment, and processing is minimized while maximizing protection from mail potentially contaminated with dangerous pathogens.

Although various embodiments of the invention have been illustrated in the accompanying drawing and described in the foregoing detailed description, it will be understood that the invention is not limited to the embodiments disclosed but, as will be appreciated by those skilled in the art, is susceptible to numerous modifications and variations without departing from the spirit and scope of the invention as hereinafter claimed. Detection and decontamination aspects of the invention could be practiced by parties other than a federal postal service, such as corporations receiving a large volume of mail which is sorted internally, or private courier services. The described process and system for disinfecting mail could also be applied to other generally flat objects, such as paper currency. Currency processing and dispensing machines are in common use. Upon adaptation of such handling systems an with e-beam scanner such as shown in FIG. 4, disinfection should be effective because currency is essentially 2-dimensional and thus only surface sterilization is needed. These and other variations are within the scope of the invention.

The invention claimed is:

1. A method of sorting mail according to the invention comprising:

receiving a batch of first mail pieces identified as unknown source mail based on the locations from which the mail was collected in an apparatus for bulk processing of the mail pieces;

receiving second mail pieces identified based on their source as having a lesser risk of contamination than the first mail pieces and keeping the second mail pieces separated from the first mail pieces until after the first mail pieces have been one of tested to determine if a potentially dangerous microorganism is present, or sterilized;

processing the batch of first mail pieces in the bulk processing apparatus by one of testing the first mail pieces to determine if a potentially dangerous microorganism is present, sterilizing the first mail pieces to destroy microorganisms on the first mail pieces, or both, while maintaining the batch of first mail pieces separate from the second mail pieces; and if no contamination is detected or if sterilization is carried out for the batch of first mail pieces, then combining the first mail pieces at a later stage of postal processing with the second mail pieces.

2. The method of claim 1, wherein processing the first mail pieces in the bulk processing apparatus comprises testing the mail pieces to determine if a potentially dangerous microorganism is present.

3. The method of claim 1, wherein processing the first mail pieces in the bulk processing apparatus comprises sterilizing the first mail pieces to destroy microorganisms on mail pieces.

4. The method of claim 1, wherein processing the first mail pieces in the bulk processing apparatus comprises testing the first mail pieces to determine if a potentially dangerous microorganism is present, and sterilizing the first mail pieces to destroy microorganisms on mail pieces only when testing indicates a potentially dangerous microorganism is likely to be present.

5. The method of claim 1, wherein the first mail pieces comprise one or more of mail collected from postal drop boxes, residences and businesses, and the second mail pieces comprise one or both of metered mail and mail from trusted mailers.

6. A method of sorting mail comprising:
receiving a batch of first mail pieces in an apparatus for bulk processing of the mail pieces;
processing the batch of first mail pieces in the bulk processing apparatus by one of testing the first mail pieces to determine if a potentially dangerous microorganism is present in the batch of first mail pieces, sterilizing the first mail pieces to destroy microorganisms on the first mail pieces, or both;
then if no contamination is detected or if sterilization is carried out, sorting the first mail pieces with second mail pieces identified based on their source as having a lesser risk of contamination than the first mail pieces together in an automated sorting machine, which second mail pieces have been identified as trusted source mail and kept separate from the first mail pieces until after the first mail pieces have been tested to determine if a potentially dangerous microorganism is present, or sterilized.

7. The method of claim 6 wherein the first mail pieces are identified as unknown source mail based on the locations from which the first mail piece were collected.

8. The method of claim 6 wherein the step of sorting the first and second mail pieces together in an automated sorting machine comprises sorting the mail pieces by destination.

9. The method of claim 6 wherein the second mail pieces comprise metered mail, the method further comprising combining the first and second mail pieces with third, trusted source mail pieces prior to sorting the mail pieces.

10. The method of claim 9 wherein trusted source mail pieces include one or more of mail generated by bulk mailers, government agencies and private mail processors.

11. A method of sorting mail comprising:
(a) collecting a plurality of first mail pieces from one or more of postal drop boxes, residences and businesses;
(b) testing the first mail pieces to determine if a potentially dangerous microorganism is present;
(c) processing the first mail pieces to separate parcels and flats from letter mail pieces;
(d) combining letter mail separated from the first mail pieces with second metered letter mail pieces;
(e) at a later stage of postal processing, combining the letter mail from step (d) with third, trusted source letter mail pieces identified as having a lesser risk of contamination than the first mail and second pieces based on their source; and
(f) sorting the combined letter mail pieces from step (f) together in an automated sorting machine.

12. The method of claim 11 wherein the first mail pieces comprise unknown source mail based on the locations from which the mail was collected.

13. The method of claim 12, wherein the second mail pieces comprise metered mail.

14. The method of claim 12, wherein the third mail pieces comprise mail originating from bulk mailers, government agencies, and private mail processors.

* * * * *